United States Patent [19]

Lee et al.

[11] Patent Number: 4,766,145

[45] Date of Patent: Aug. 23, 1988

[54] ANTIHYPERCHOLESTEROLEMIC COMPOUNDS

[75] Inventors: Ta J. Lee, Lansdale; Clarence S. Rooney, Worcester; William F. Hoffman, Lansdale, all of Pa.

[73] Assignee: Merck & Co., Inc., Rahway, N.J.

[21] Appl. No.: 859,525

[22] Filed: May 5, 1986

[51] Int. Cl.[4] .............. A61K 31/785; A61K 31/365; C07D 309/30

[52] U.S. Cl. ................... 514/460; 514/824; 549/292

[58] Field of Search .............. 514/824, 460; 549/292

[56] References Cited

U.S. PATENT DOCUMENTS

| | | | |
|---|---|---|---|
| 3,308,020 | 3/1967 | Wolf et al. | 514/824 |
| 3,983,140 | 9/1976 | Endo et al. | 549/292 |
| 4,154,952 | 5/1979 | Schultz | 560/96 |
| 4,346,227 | 8/1982 | Terahara et al. | |
| 4,444,784 | 4/1984 | Hoffman et al. | |
| 4,448,979 | 5/1984 | Terahara et al. | |
| 4,517,373 | 5/1985 | Terahara et al. | |

FOREIGN PATENT DOCUMENTS 59-122483A 7/1984 Japan .

OTHER PUBLICATIONS

Chemical Abstract, 87:22516w.
1 Chemical Abstract 86:720290g
1 Chemical Abstract 95:42437q.

*Primary Examiner*—Norma S. Milestone
*Attorney, Agent, or Firm*—Melvin Winokur; Joseph F. DiPrima

[57] ABSTRACT

Novel 3-hydroxy-3-methylglutaryl-Coenzyme A(HMG-CoA) reductase inhibitors, which are useful as antihypercholesterolemic agents and are represented by the following general structural formulae (I) and (II)

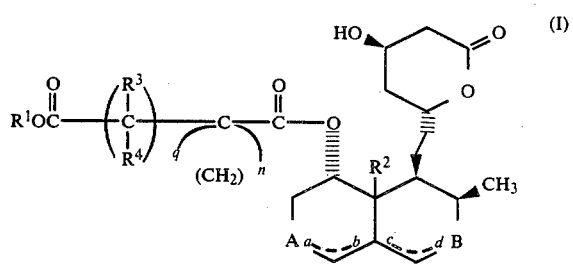

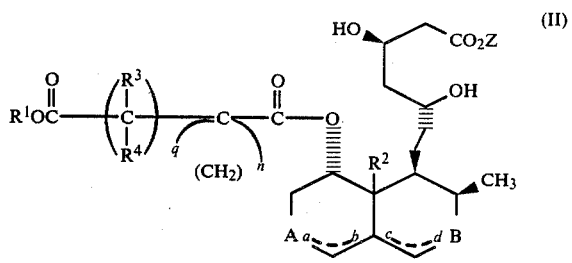

and pharmaceutically acceptable salts of the compound (II) in which Z is hydrogen are disclosed.

13 Claims, No Drawings

ANTIHYPERCHOLESTEROLEMIC COMPOUNDS

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e., several grams at a time and they are not very palatable.

There are agents known, however, that are very active antihyperchlolesterolemic agents that function by limiting cholesterol biosynthesis by inhibiting the enzyme, HMG-CoA reductase. These agents include the natural fermentation products compactin and mevinolin and a variety of semisynthetic and totally synthetic analogs thereof. The naturally occurring compounds and their semisynthetic analogs have the following general structural formulae:

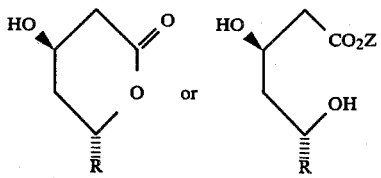

wherein:
Z is hydrogen, $C_{1-5}$ alkyl or $C_{1-5}$ alkyl substituted with a member of the group consisting of phenyl, dimethylamino, or acetylamino;
R is

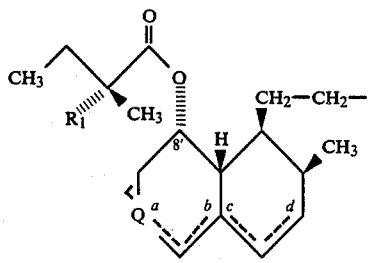

wherein
Q is

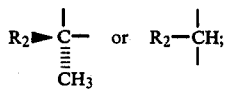

$R_2$ is H or OH;
$R_1$ is hydrogen or methyl; and a, b, c, and d represent optional double bonds, especially where b and d represent double bonds or a, b, c, and d are all single bonds.

U.S. Pat. No. 4,517,373 discloses semi-synthetic compounds represented by the above general formula wherein R is

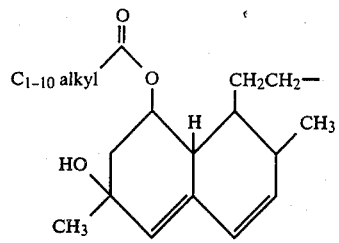

and

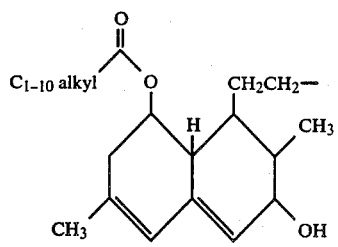

U.S. Pat. No. 4,346,227 and U.S. Pat. No. 4,448,979 also disclose semi-synthetic compounds represented by the above general formula wherein R is

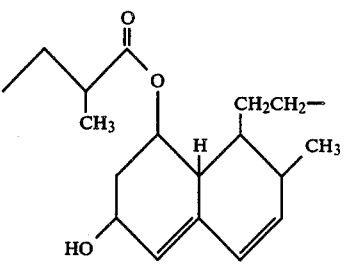

and

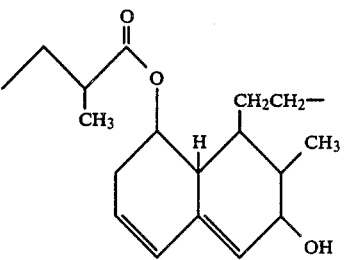

Japanese unexamined patent application No. J59-122,483-A discloses a semi-synthetic compound represented by the above general formula wherein R is

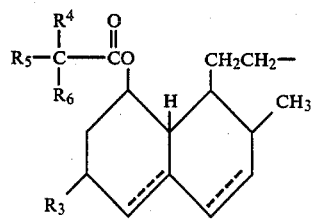

in which $R_3$ is hydrogen or methyl; $R_4$ is hydrogen, halogen or haloalkyl; $R_5$ is hydrogen, halogen or loweralkyl and $R_6$ is halogen, $N_3$, hydroxy, thio, amino, lower alkoxy, lower alkylthio and aralkylthio.

U.S. Pat. No. 4,444,784 discloses 8'-acyloxy derivatives of compactin, mevinolin and the dihydro and tetrahydro analogs thereof. Generically disclosed are the compounds represented by the above general formula wherein R is

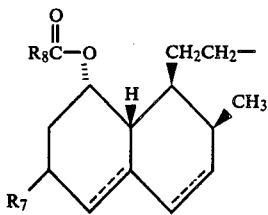

in which $R_7$ is hydrogen or methyl and $R_8$ is $C_{3-10}$ cycloalkyl.

SUMMARY OF THE INVENTION

This invention relates to novel compounds which are HMG-CoA reductase inhibitors and are useful as antihypercholesterolemic agents. Specifically, the compounds of this invention are semi-synthetic analogs of compactin, mevinolin, and the dihydro and tetrahydro analogs thereof which possess a specifically substituted cycloalkyl 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

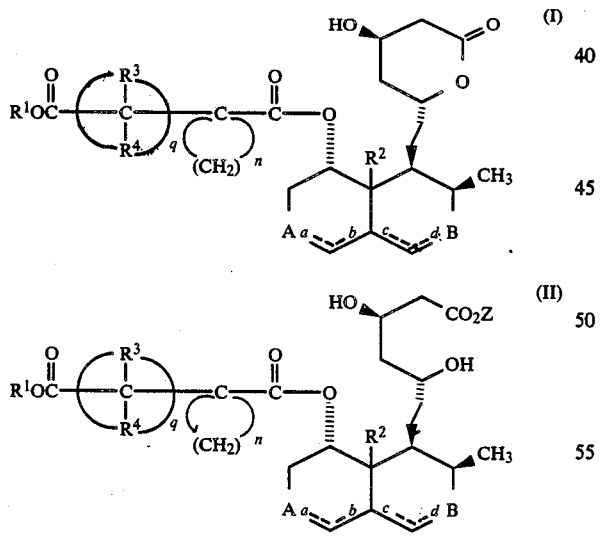

wherein:
q is 0 to 5;
n is 2 to 7;
$R^1$ is $C_{1-6}$ alkyl,
$R^2$ is hydrogen or hydroxy;
$R^3$ and $R^4$ independently are hydrogen, $C_{1-3}$ alkyl, $C_{3-7}$ cycloalkyl, phenyl or phenyl substituted with X and Y and when q is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl;
A is

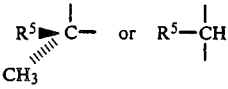

in which $R^5$ is hydrogen or hydroxy;
B is

in which $R^6$ is hydrogen or hydroxy;
a, b, c and d represent single bonds, one of a, b, c or d represents a double bond or both a and c or both b and d represent double bonds, provided that when a is a double bond, A is

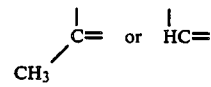

and when d is a double bond, B is

and
X and Y independently are hydrogen, halogen, trifluoromethyl, $C_{1-3}$ alkyl, nitro, cyano or a group selected from:
(a) $R^7O(CH_2)_m$ in which m is 0 to 3 and $R^7$ is hydrogen, $C_{1-3}$ alkyl or hydroxy-$C_{2-3}$ alkyl;
(b)

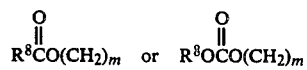

in which $R^8$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(-hydroxy-$C_{2-3}$ alkyl)amino-$C_{1-3}$ alkyl;
(c)

in which $R^9$ is hydrogen, $C_{1-3}$ alkyl, hydroxy-$C_{1-3}$ alkyl, $C_{1-3}$ alkoxy-$C_{1-3}$ alkyl, phenyl or naphthyl;
(d) $R^{10}R^{11}N(CH_2)_m$,

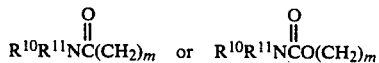

in which $R^{10}$ and $R^{11}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl;

(e) $R^{12}S(O)_p(CH_2)_m$ in which p is 0 to 2 and $R^{12}$ is hydrogen, $C_{1-3}$ alkyl, amino, $C_{1-3}$ alkylamino or di($C_{1-3}$ alkyl)amino;

Z is hydrogen, $C_{1-5}$ alkyl or $C_{1-5}$ alkyl substituted with a group selected from phenyl, dimethylamino or acetylamino; and pharmaceutically acceptable salts of the compounds of the formula (II) in which Z is hydrogen.

One embodiment of this invention is the class of compounds of the formula (I) and (II) wherein q is 0, $R^2$, $R^5$ and $R^6$ are hydrogen and a, b, c and d represent single bonds or both b and d represent double bonds. Particular compounds of this embodiment are those of the formulae (I) and (II) wherein n is 2 to 5.

Illustrative of this embodiment when n is 2 is the compound, 6(R)-[2-[8(S)-[1-Ethoxycarbonylcyclopropanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

Illustrative of this embodiment when n is 3 is the compound, 6(R)-[2-[8(S)-[1-Ethoxycarbonylcyclobutanecarbonyloxy]-2(S),6(R)-dimethyl-1,2,6,7,8,8a(R)-hexahydronaphthyl-1-(S)]ethyl]-4(R)-hydroxy-3,4,5,6-tetrahydro-2H-pyran-2-one.

Another embodiment of this invention is the class of compounds of the formula (II) wherein Z is hydrogen or $C_{1-5}$ alkyl aand pharmaceutically acceptable salts of the compounds of the formula (II) wherein Z is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)amintoethane, and tetramethylammonium hydroxide.

The compounds of formula (I) are conveniently prepared from compactin, mevinolin, or the appropriate dihydro or tetrahydro analog thereof via the following general synthetic pathway:

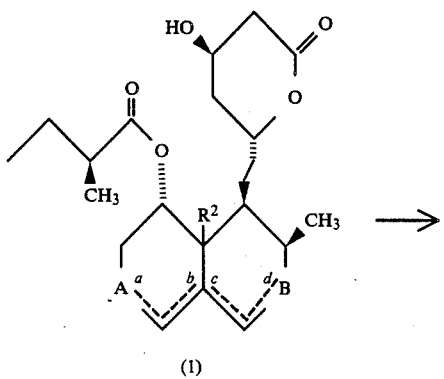

(1)

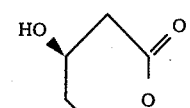

(2)

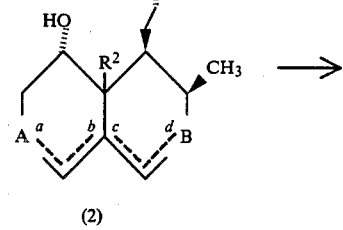

(3)

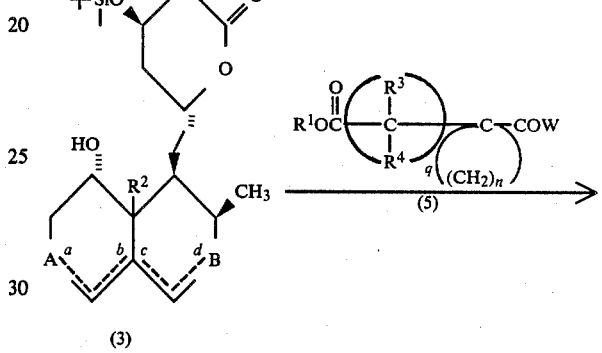

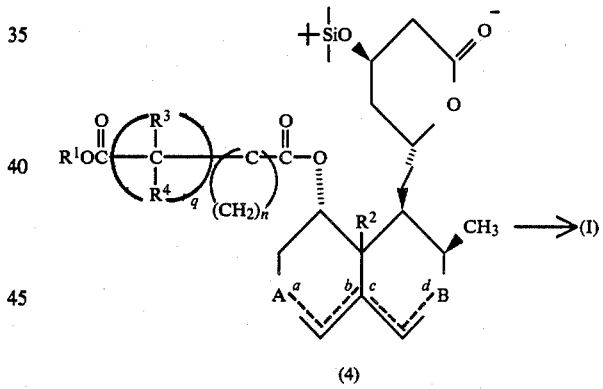

(4)

The starting materials compactin, mevinolin, and their dihydro and tetrahydro analogs are readily available or may be prepared according to fermentation procedures disclosed in U.S. Pat. No. 3,983,140, U.S. Pat. No. 4,049,495, U.S Pat. No. 4,231,938, U.S. Pat. No. 4,294,846, U.S. Pat. No. 4,343,814, and the hydrogenation procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784 to give the compounds of the formula (3).

Acylation of the 8-hydroxy group of the compound (3) is accomplished under suitable conditions utilizing the appropriately substituted acids or acid halides of the formula (5) wherein n, $R^1$, $R^3$, and $R^4$ are as described above and W is hydroxy or halogen, especially chloro or bromo. The protecting group of the compound of the formula (4) is removed utilizing suitable conditions to afford the compounds of the formula (I). For the compounds of this invention wherein the polyhydronaphthyl moiety is substituted with a hydroxy group, the compound of the formula (4) is subject to a microbiological hydroxylation after the removal of the protecting groups utilizing the general procedures disclosed in U.S. Pat. No. 4,346,227, U.S. Pat. No. 4,448,979, U.S. Pat. No. 4,517,373 and Japanese Patent Application No. J-60-130,548.

The appropriate substituted acids or acid halides of the formula (5) are commercially available or prepared from known starting materials utilizing standard chemical transformations.

The compounds of the formula (II) wherein Z is hydrogen or a pharmaceutcially acceptable salt thereof are readily prepared by the mild basic hydrolysis of the lactone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The compounds of this invention are useful as antihyperchlolesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 20 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in J. Med. Chem., 28, P. 347–358 (1985) and described below:

Isolation of HMG-CoA Reductase.

Male Holtzman Sprague-Dawley rate (225–250 g) were kept on reversed lighting and fed Purina rat chow containing 3% chlolestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsome by the method of Heller and Shrewsbury [J. Biol. Chem., 1976, 251, 3815], and purified through the second ammonium sulfate precipitation step as described by Kleinsek et al. [Proc. Natl. Acad. Sci. USA, 1977, 74, 7431]. The enzyme preparation was tested for HMG-CoA reductase potency and diluted with 100 mM phosphate buffer (pH 7.2) so that 100 μL of the enzyme solution, when added to the assay control, gave a value of 50,000–60,000 dpm. The enzyme preparation was stored at −80° C.

HMG-CoA Reductase Inhibition Assay.

The assay is essentially the procedure of Shefer et al., [J. Lipid Res., 1972, 13, 402]. The complete assay medium contained the following in a total volume of 0.8 mL: phosphate buffer, pH 7.2, 100 mM; $MgCl_2$, 3 mM; NADP, 3 mM; glucose 6-phosphate, 10 mM; glucose-6-phosphate dehydrogenase, 3 enzyme units; reduced glutathione, 50 mM; HMG-CoA (glutaryl-3-$^{14}C$, New England Nuclear), 0.2 mM (0.1 μCi); and partially purified enzyme stock solution, 100 μL.

Test compounds or compactin (after first being converted to the sodium salt of their dihydroxy acid form in situ by addition of 1N NaOH (1 equiv)) were added to the assay system in 10-μL volumes at multiconcentration levels. After a 40-minute incubation at 37° C. with shaking and exposure to air, the reaction was stopped by the addition of 0.4 mL of 8N HCl. After an additional 30-minute incubation period at 37° C. to ensure the complete lactonization of mevalonic acid to mevalonolactone, 0.2 mL of the mixture was added to an 0.5×5.0 cm column containing 100-200-mesh Bio-Rex 5, chloride form (Bio-Rad), wetted with distilled water, as described by Alberts et al. [J. Proc. Natl. Acad. Sci. U.S.A., 1980, 77, 3957]. The unreacted [$^{14}C$]HMG-CoA was absorbed on the resin and the [$^{14}C$]mevalonolacetone was eluted with distilled water (2×1 mL) directly into 7-mL scintillation vials. Five milliliters of Aquasol-2 (New England Nuclear) was added to each vial, and radioactivity was measured in a Packard Tri Carb Prias scintillation counter. $IC_{50}$ values were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG-CoA reductase inhibitory activities of the claimed compounds tabulated below are a number of the claimed compounds and the relative potencies for said compounds.

TABLE 1

| T | Relative Potency[1] |
|---|---|
| $C_2H_5OC(O)-C(CH_2)(CH_2)-$ | 11 |

TABLE 1-continued

[Chemical structure diagram showing a decalin-based compound with H, CO₂H, OH, T—CO, CH₃, CH₃ substituents]

| T | Relative Potency[1] |
|---|---|
| $C_2H_5OC-C\underset{CH_2}{\overset{O}{\underset{\diagdown}{\diagup}}}\underset{}{\overset{}{\underset{CH_2}{\diagdown}}}CH_2$ | 65 |

[1] Relative to compactin which was arbitrarily assigned a value of 100.

Included within the scope of this invention is the method of treating arteriosclerosis, familial hyperchlolesterolemia or hyperlipidemia which comprises administering to a subject in need of such treatment a nontoxic, therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(1-Ethoxycarbonylcyclopropanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 1-Ethoxycarbonylcyclopropanecarboxylic acid (1a)

A solution of sodium hydroxide (2.15 g, 54 mmol) in water (15 ml) was added dropwise to a stirred solution of diethyl 1,1-cyclopropanedicarboxylate (10 g, 54 mmol) in ethanol (30 ml) while the temperature was maintained below 25° C. After the completion of the addition, the resulting mixture was stirred at room temperature for 60 hours. Most of ethanol was removed by evaporation in vacuo and the residue was diluted with brine, acidified with 6N hydrochloric acid and extracted with diethyl ether. The extract was dried over magnesium sulfate, filtered and concentrated. The residue was purified by distillation to give the title compound (bp 66°–9° C./0.15 mm) as a viscous oil.

(b) Preparation of 1-Ethoxycarbonylcyclopropanecarbonyl chloride

Oxalyl chloride (6.0 g, 47 mmol) was added to a stirred mixture of 1-ethoxycarbonylcyclopropane carboxylic acid (1a) (6 g, 38 mmol) in benzene (25 ml) plus two drops of dimethylformamide. After the gas evolution ceased, the stirring was continued at room temperature for another hour. The reaction mixture was concentrated. The residue was purified by distillation. A fraction collected at 91°–2° C./15 mm was redistilled to give the desired product.

(c) Preparation of 6(R)-[2-[8(S)-(1-Ethoxycarbonylcyclopropanecarbonyloxy)-2(S), 6(R)-dimethyl-1,2,6,7,8,8a(R)-hexahydronaphthyl-1(S)]ethyl]-4(R)-tert-butyldimethylsilyloxy-3,4,5,6-tetrahydro-2H-pyran-2-one (1c)

1-Ethoxycarbonylcyclopropanecarbonyl chloride (1b) (0.728 g, 4.14 mmol) was added in one portion to a stirred mixture of 6(R)-[2-[8(S)-hydroxy-2(S), 6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (0.6 g, 1.38 mmol) and 4-dimethylaminopyridine (0.513 g, 4.2 mmol) in pyridine (8 ml) under the cooling of a cold water bath. The resulting mixture was stirred at room temperature for 5 hours, then poured into cold water and extracted with diethyl ether. This extract was washed successively with diluted hydrochloric acid, water and 5% sodium bicarbonate, dried over magnesium sulfate, filtered and evaporated. The residue was purified by flash chromatography on a column of silica gel. Eluted with $CH_2Cl_2$:acetone (250:1) A crude sample of the title compound which was repurified by flash chromatography on a column of silica gel eluted with $CH_2Cl_2$:acetone (200:1) to offer pure title compound as a colorless viscous oil: nmr (CDCl$_3$) δ=0.07 (6H, s), 0.9 (9H, s), 1.07 (3H, d, J=7 Hz), 1.21 (3H, t, J=7 Hz), 2.58 (2H, d, J=4 Hz), 4.11 (2H, q, J=7 Hz), 4.28 (1H, m), 4.61 (1H, m), 5.3–5.6 (2H, m), 5.74 (1H, d of d, J=10, 5 Hz), 6.00 (1H, d, J=10 Hz).

(d) 6(R)-[2-[8(S)-(1-Ethoxycarbonylcyclopropanecarbonyloxy)-2(S),6(R)-dimethyl-1,2,6,7,8,8a(R)hexahydronaphthyl-1(S)]ethyl]-4(R)-hydroxy-3,4,5,6-tetrahydro-2H-pyrane-2-one Tetra-n-butylammonium fluoride solution (0.5 ml, 1M in tetrahydrofuran) was added to a stirred solution of 6(R)-[2-[8(S)-(1-ethoxycarbonylcyclopropanecarbonyloxy)-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (1c) (56 mg. 0.097 mmol) and acetic acid (46 μl, 0.8 mmol) in tetrahydrofuran (2 ml). The resulting mixture was stirred at room temperature for 18 hours, then poured into cold water and extracted with diethyl ether. This extract was washed with water and aqueous sodium bicarbonate, dried over magnesium sulfate and concentrated. The residue was purified by preparative thin layer chromatography to yield the desired product as a off-white solid:mp 86°–8° C.; nmr (CDCl$_3$) δ=0.92 (3H, d=7 Hz), 1.10 (3H, d, J=7 Hz), 1.24 (3H, t, J=7 Hz), 2.65 (1H, m of d, J=17 Hz), 2.78 (1H, d of d, J=17, 5 Hz), 4.15 (2H, d of q, J=7, 2 Hz), 4.40 (1H, m), 4.67 (1H, m) 5.40 (1H, m), 5.53 (1H, m), 5.80 (1H, d of d, J=10, 5 Hz), 6.00 (1H, d, J=10 Hz).

Anal. Calcd for $C_{26}H_{36}O_7$: C, 67.80; H; 7.88. Found: C, 67.54; H, 8.14.

EXAMPLE 2

Preparation of
6(R)-[2-8(S)-(1-Ethoxycarbonylcyclobutanecarbonyloxy)-2(S),6(R)-dimethyl-1,2,6,7,8,8a-(R)-hexahydronaphthyl-1(S)]ethyl]-4(R)-hydroxy-3,4,5,6-tetrahydro-2H-pyrane-2-one (2)

(a) 1-Ethoxycarbonylcyclobutanecarboxylic Acid (2a)

Sodium hydroxide (1N, 22.5 mmol) was added dropwise (1 drop for every 20 seconds) to a stirred solution of diethyl 1,1-cyclobutanedicarboxylate (4.5 g, 22.5 mmol) in ethanol (20 ml). The resulting mixture was stirred at room temperature for 6 hours, then concentrated by evaporation to a volume of about 10 ml. This residue was shaken with diethyl ether and the aqueous layer was separated. This aqueous was acidified with 12N hydrochloric acid while the temperature was kept below 10° C. The resulting mixture was extracted with diethyl ether (3×50 ml). The combined extracts were dried over magnesium sulfate, filtered and evaporated to yield the desired product as a colorless oil.

(b) 6(R)-[2-[8(S)-(1-Ethoxycarbonylcyclobutanecarbonyloxy)-2(S),6(R)-dimethyl-1,2,6,7,8,8a-(R)-hexahydronaphthyl-1(S)]ethyl]-4(R)-(tert-butyldimethylsilyloxy)-3,4,5,6-tetrahydro-2H-pyran-2-one (2b)

A solution of 2,6-dichloro-4-methoxy-1,3,5-triazine (0.9 g, 5 mmol) in methylene chloride (10 ml) was added dropwise to a stirred solution of 1-ethoxycarbonylcyclobutane carboxylic acid (2a) (0.86 g, 5 mmol), and N-methylmorpholine (0.55 ml, 5 mmol) in methylene chloride (10 ml) at −5° C. The resulting mixture was stirred at −5° C. for 2 hours and then added to a solution of 6(R)-[2-[8(S)-hydroxy-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (1.08 g, 2.5 mmol) in methylene chloride (10 ml). The resulting mixture was then heated at reflux for 22 hours. The reaction mixture was cooled, diluted with diethyl ether (250 ml), then washed successively with water (25 ml), 1N hydrochloric acid, water (25 ml), saturated sodium bicarbonate (25 ml) and brine (50 ml), dried over magnesium sulfate, filtered and evaporated to yield a yellow oily residue. This residue was purified by flash column chromatography on silica gel eluted first with methylene chloride:acetone (100:1), then with methylene chloride:acetone (50:1) to afford the desired product as an oil which was used in the next reaction without further purification.

(c) 6(R)-[2-[8(S)-(1-Ethoxycarbonylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Tetra-n-butylammonium fluoride solution (1M in tetrahydrofuran 2.75 ml, 2.75 mmol) was added to a solution of 6(R)-[2-[8(S)-[1-ethoxycarbonylcyclobutanecarbonyloxy]-2(S),6(R)dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (2b) (0.54 g, 0.92 mmol) and acetic acid (0.21 ml, 3.7 mmol) in tetrahydrofuran (25 ml). The resulting mixture was stirred at room temperature for 18 hours, then at 70° C. for 2 hours. The reaction mixture was cooled and diluted with diethyl ether (200 ml). The resulting mixture was washed successively with water (25 ml), 1N hydrochloric acid (10 ml), brine (25 ml), saturated aqueous sodium bicarbonate (25 ml) and brine (50 ml), dried over magnesium sulfate and evaporated to yield a viscous oil which was purified by flash column chromatography on a column of silica gel eluted first with methylene chloride:acetone (9:1), then with methylene chloride:acetone (4:1) to afford an oily residue. This residue is rechromatographed on a silica gel column, eluted with hexane:2-propanol (9:1) to give a residue which was subsequently purified by preparative HPLC (Partisil 5 RAC column, eluant:2.4% 2-propanol in hexane, flow rate:10 ml/minute) to afford the pure title compound as a gummy oil.

Anal. Calcd. for $C_{27}H_{38}O_7 \cdot H_2O$ C, 65.83; H, 8.18. Found: C, 65.48; H, 8.51.

EXAMPLE 3 to 13

Utilizing the general procedures from Examples 1 and 2 the following compounds are prepared from the appropriate starting materials:

TABLE 2

| Compound | T | $T_1$ | b | c | d |
|---|---|---|---|---|---|
| 3 | $CH_3O-\overset{O}{\underset{\|}{C}}-\overset{CH_2}{\underset{CH_2}{\diagdown\diagup}}C-$ | H | db | — | db |
| 4 | $i\text{-}C_3H_7O\overset{O}{\underset{\|}{C}}-\overset{CH_2}{\underset{CH_2}{\diagdown\diagup}}C-$ | $CH_3$ | — | — | — |
| 5 | $n\text{-}C_5H_{12}O\overset{O}{\underset{\|}{C}}-C(CH_2CH_2CH_2)-$ | $CH_3$ | — | db | — |
| 6 | $CH_3O\overset{O}{\underset{\|}{C}}-C(CH_2CH_2CH_2)-$ | H | db | — | db |
| 7 | $C_2H_5O\overset{O}{\underset{\|}{C}}-C(CH_2CH_2CH_2CH_2)-$ | $CH_3$ | — | — | — |
| 8 | $n\text{-}C_3H_7O\overset{O}{\underset{\|}{C}}-C(CH_2CH_2CH_2CH_2)-$ | H | db | — | — |
| 9 | $CH_3O\overset{O}{\underset{\|}{C}}-C(CH_2CH_2CH_2CH_2CH_2)-$ | $CH_3$ | db | — | — | db = double bond

TABLE 3

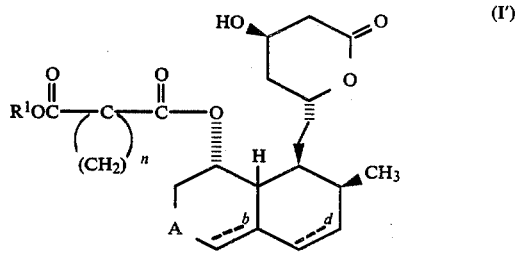

| Compound | T | T₁ | T₂ | T₃ | a | b | c | c |
|---|---|---|---|---|---|---|---|---|
| 10 | $C_2H_5OC\underset{CH_2\text{——}CH_2}{\overset{O}{\overset{\|}{-C-}}}$ | OH | H | H | — | db | — | db |
| 11 | $CH_3O\overset{O}{\overset{\|}{C}}-\underset{\underset{CH_2}{\overset{CH_2}{\|}}\underset{\|}{\overset{CH_2}{CH_2}}}{C}$ | OH | CH₃ | H | — | db | — | db |
| 12 | $i\text{-}C_3H_7O\overset{O}{\overset{\|}{C}}-\underset{CH_2\text{——}CH_2}{\overset{CH_2\ \ CH_2}{C}}$ | H | — | OH | db | — | db | — |
| 13 | $C_2H_5O\overset{O}{\overset{\|}{C}}-\underset{\underset{CH_2}{\overset{CH_2}{\|}}\underset{\|}{\overset{CH_2}{CH_2}}}{C}$ | CH₃ | — | OH | — | — | — | — | db = double bond

EXAMPLE 14

Preparation of Alkali and Alkaline Earth Salts of Compound II

To a solution of 42 mg of the lactone from Example 1(d) in 2 ml of ethanol is added 1 ml of aqueous NaOH (1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 15

Preparation of Methyl Ester of Compound II

To a solution of 400 mg of the lactone from Example 1(d) in 100 ml of absolute methanol is added 10 ml 0.1M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amyl alcohol, isoamyl alcohol, 2-dimethylaminoethanol, benzyl alcohol, phenethanol, 2-acetamidoethanol, and the like, the corresponding esters are obtained.

EXAMPLE 16

Preparation of Free Hydroxy Acids

The sodium salt of the compound II from Example 14 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 17

As a specific embodiment of a composition of this invention, 20 mg of the lactone from Example 1(d) is formulated with sufficient finely divided lactose to provide a total amount of 580 to 590 mg to fill a size 0 hard gelatin capsule.

What is claimed is:

1. A compound represented by the following general structural formula (I'):

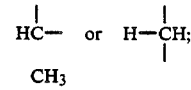

wherein:
n is 2 to 7;
R¹ is $C_{1-6}$ alkyl,
A is $$\underset{CH_3}{\overset{\|}{HC-}} \quad \text{or} \quad \underset{}{\overset{\|}{H-CH;}}$$

b and d represent single bonds, or both b and d represent double bonds.

2. A compound of claim 1 wherein n is 2 to 5.
3. A compound of claim 2 wherein n is 2.
4. A compound of claim 3 which is 6(R)-[2-[8(S)-(1-Ethoxycarbonylcyclopropanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.
5. A compound of claim 2 wherein n is 3.
6. A compound of claim 5 which is 6(R)-[2-[8(S)-(1-Ethoxycarbonylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.
7. A hypocholesterolemic, hypolipidemic pharmaceutical composition comprising a nontoxic therapeutically effective amount of a compound of claim 1 and a pharmaceutically acceptable carrier.
8. A composition according to claim 7 wherein n is 2 to 5.

9. A composition according to claim 8 wherein the therapeutically active ingredient is selected from the group consisting of:

6(R)-[2-[8(S)-(1-Ethoxycarbonylcyclopropanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

6(R)-[2-[8(S)-(1-Ethoxycarbonylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

10. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

11. A method of inhibiting cholesterol biosynthesis comprising the administration to a subject in need of such treatment a nontoxic therapeutically effective amount of a compound of claim 1.

12. A method of claim 11 wherein n is 2 to 5.

13. A method of claim 12 wherein the therapeutically active ingredient is selected from the group consisting of:

6(R)-[2-[8(S)-(1-Ethoxycarbonylcyclopropanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

6(R)-[2-[8(S)-(1-Ethoxycarbonylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2one.

* * * * *